(12) United States Patent
Wieczorek et al.

(10) Patent No.: US 8,891,726 B2
(45) Date of Patent: Nov. 18, 2014

(54) MULTIPLE-SOURCE IMAGING SYSTEM WITH FLAT-PANEL DETECTOR

(75) Inventors: Herfried Wieczorek, Aachen (DE); Gereon Vogtmeier, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 912 days.

(21) Appl. No.: 12/864,880

(22) PCT Filed: Feb. 2, 2009

(86) PCT No.: PCT/IB2009/050407
§ 371 (c)(1),
(2), (4) Date: Jul. 28, 2010

(87) PCT Pub. No.: WO2009/101543
PCT Pub. Date: Aug. 20, 2009

(65) Prior Publication Data
US 2010/0322498 A1    Dec. 23, 2010

Related U.S. Application Data

(60) Provisional application No. 61/028,530, filed on Feb. 14, 2008.

(51) Int. Cl.
*G06K 9/00* (2006.01)
*A61B 6/00* (2006.01)
*A61B 6/03* (2006.01)

(52) U.S. Cl.
CPC .............. *A61B 6/4007* (2013.01); *A61B 6/032* (2013.01); *A61B 6/4014* (2013.01); *A61B 6/4233* (2013.01); *A61B 6/4447* (2013.01); *A61B 6/4028* (2013.01); *A61B 6/4488* (2013.01)
USPC ................................ 378/9; 382/131; 382/132

(58) Field of Classification Search
CPC ................................................... A61B 6/4007
USPC ................................ 378/9; 382/131, 132
See application file for complete search history.

(56) References Cited

U.S. PATENT DOCUMENTS 6,236,708 B1    5/2001   Lin et al.
6,385,292 B1 *  5/2002   Dunham et al. .............. 378/122
(Continued)

OTHER PUBLICATIONS

Zhang, J., et al.; Multiplexing radiography using a carbon nanotube based x-ray source; 2006; Applied Physics Letters; 89:64106.
(Continued)

*Primary Examiner* — Hoon Song
*Assistant Examiner* — Danielle Fox

(57) ABSTRACT

When performing nuclear (e.g., SPECT or PET) and CT scans on a patient, an imaging system (10) includes three or more carbon nanotube x-ray sources (20) are circumferentially spaced along an arc of a rotatable gantry (16) that spans a distance larger than a maximum cross-sectional dimension of a section of a patient (14) to be imaged. The x-ray sources are sequentially pulsed to emit x-rays for scanning a section of a patient (14) including a volume of interest (VOI) (13). Only one source (20) is in an ON state at a time to create a duty cycle, which reduces cooling time for the respective sources as well as radiation dose to the subject. X-rays traversing the patient (14) are received at a flat panel x-ray detector (22) that has a width smaller than the maximum cross-sectional dimension, which further reduces the weight and size of the system (10).

23 Claims, 3 Drawing Sheets

(56) References Cited

U.S. PATENT DOCUMENTS

| | | | |
|---|---|---|---|
| 6,421,412 B1* | 7/2002 | Hsieh et al. | 378/9 |
| 7,227,924 B2* | 6/2007 | Zhou et al. | 378/10 |
| 7,433,433 B2* | 10/2008 | Wilhelmsson et al. | 375/350 |
| 2003/0128801 A1* | 7/2003 | Eisenberg et al. | 378/19 |
| 2005/0189494 A1 | 9/2005 | Conwell | |
| 2005/0190878 A1* | 9/2005 | De Man et al. | 378/9 |
| 2006/0233295 A1* | 10/2006 | Edic et al. | 378/4 |
| 2006/0245537 A1* | 11/2006 | Bakai et al. | 378/9 |
| 2007/0009088 A1* | 1/2007 | Edic et al. | 378/62 |
| 2007/0221850 A1 | 9/2007 | Panin et al. | |
| 2008/0013674 A1* | 1/2008 | Zhang et al. | 378/9 |
| 2010/0290584 A1* | 11/2010 | Vesel et al. | 378/9 |
| 2011/0311019 A1* | 12/2011 | Ribbing et al. | 378/9 |

OTHER PUBLICATIONS

Cellar, A., et al.; Reconstruction of Multiple Line Source Attenuation Maps; 1996; Nuclear Science Symposium Conference Record; IEEE; vol. 2; pp. 1420-1424.

Lalush, D. S.; Feasibility of Transmission Micro-CT with Two Fan-Beam Sources; 2004; IEEE EMBS; vol. 2; pp. 1283-1286.

Zhang, J., et al.; A nanotube-based field emission x-ray source for microcomputed tomography; 2005; Review of Scientific Instruments; 76:094301.

Zhang, J., et al.; Stationary scanning x-ray source based on carbon nanotube field emitters; 2005; Applied Physics Letters; 86:184104.

\* cited by examiner

MULTIPLE-SOURCE IMAGING SYSTEM WITH FLAT-PANEL DETECTOR

CROSS REFERENCE TO RELATED APPLICATIONS

This application claims the benefit of U.S. provisional application Ser. No. 61/028,530 filed Feb. 14, 2008, which is incorporated herein by reference.

The present innovation finds particular application in diagnostic imaging systems, particularly involving cone-beam computed tomography (CT). However, it will be appreciated that the described technique may also find application in hybrid or other medical scenarios, or other medical techniques.

In CT scanning, data is typically collected across an entire crossection, e.g., torso, of an imaged patient. If irradiation and data collection were focused down to a region of interest within the torso, the reconstructed image would have artifacts due to missing data, caused by truncation of the regions surrounding the region of interest. Accordingly, CT scanners typically use a detector that extends sufficiently in the circumferential direction in which an x-ray beam that spans the widest portion of the patient's torso is fully detected.

There is an interest in using flat-panel CT detectors, particularly in combined nuclear/CT systems. However, the flat-panel detectors are too small and can only receive radiation from a source that has spanned about half the width of the patient's torso. For instance, while a CT detector has a typical circumferential length of 100 cm, flat panels typically have a maximum length of about 40 cm. Others have addressed this problem by collecting half of the patient data during a first 180° of rotation and a second half during the subsequent 180° of rotation. This was disadvantageous in that it required a complete revolution to collect a data set, errors could occur in interfacing the two data sets where they meet, and potential scatter issues and movement artifacts arose.

In rotating anode x-ray tubes, the focal spot is often moved back and forth rapidly between two nearby locations on the anode, e.g., a half a detector width, to improve resolution.

Others have proposed stereo x-ray systems with a pair of full size rotating anode x-ray tubes mounted closely adjacent each other on the rotating gantry, e.g. about 10-20 cm apart. Each of the x-ray tubes generates a fan beam which spans the full patient torso and is detected by a full-sized detector on the opposite side. These two x-ray tubes are gated alternately ON and OFF such that offset sets of data are collected substantially concurrently. While these systems have been proposed, constructing such a system has proved elusive due to the large size and weight of the rotating anode x-ray tubes and their associated cooling systems. That is, each of the x-ray tubes is typically encased in a housing, through which cooling fluid is circulated from a cooling fluid reservoir. The cooling fluid from the housing is cooled by a heat exchanger before returning to the reservoir. Because current CT scanners have only enough room on the rotating gantry for a single x-ray tube and its associated cooling system (which takes up a large portion of the space available on the rotating gantry), doubling the size of this required real estate has proved problematic. Moreover, the x-ray tube and associated cooling equipment is heavy, raising mechanical issues concerning balance, bearings, and the like. Further, removing heat from a rotating gantry is also difficult. Doubling the capacity to supply a cooling fluid to the heat exchanger is also problematic.

The present application provides new and improved hybrid nuclear medicine/CT systems and methods that improving image acquisition and reconstruction time, which have the advantages of improving patient scan speed and quality, and which overcome the above-referenced problems and others.

In accordance with one aspect, a patient imaging system includes a plurality of circumferentially-spaced x-ray sources mounted on a rotatable gantry, and flat-panel X-ray detector mounted on the gantry substantially opposite the x-ray sources. The x-ray sources are sequentially pulsed to generate a continuous x-ray swath across a section of a patient including a volume of interest (VOI) as the gantry is rotated around the VOI during computed tomography (CT) acquisition.

In accordance with another aspect, a method of CT imaging includes sequentially pulsing a plurality of circumferentially-spaced x-ray sources coupled to a rotatable gantry to generate a continuous swath of x-ray across a transverse section of a patient that includes a VOI, receiving x-rays at a flat panel detector coupled to the gantry opposite the x-ray sources to acquire CT scan data, and reconstructing the CT scan data into CT image data.

In accordance with yet another aspect, an apparatus for CT imaging includes means for sequentially pulsing a plurality of circumferentially-spaced CNT x-ray sources coupled to a rotatable gantry to generate a continuous x-ray across a VOI, means for receiving x-rays a to acquire CT scan data, and means for reconstructing the CT scan data into CT image data.

One advantage is that data acquisition speed is increased.

Another advantage resides in the use of small, particularly flat panel, detectors.

Another advantage resides in radiation dose reduction.

Another advantage resides in adaptability of the system to accommodate different subject sizes.

Another advantage resides in improved motion correction.

Another advantage resides in reduced x-ray smearing.

Another advantage resides in reduced system cost and weight.

Still further advantages of the subject innovation will be appreciated by those of ordinary skill in the art upon reading and understanding the following detailed description.

The innovation may take form in various components and arrangements of components, and in various steps and arrangements of steps. The drawings are only for purposes of illustrating various aspects and are not to be construed as limiting the invention.

Figure 1:
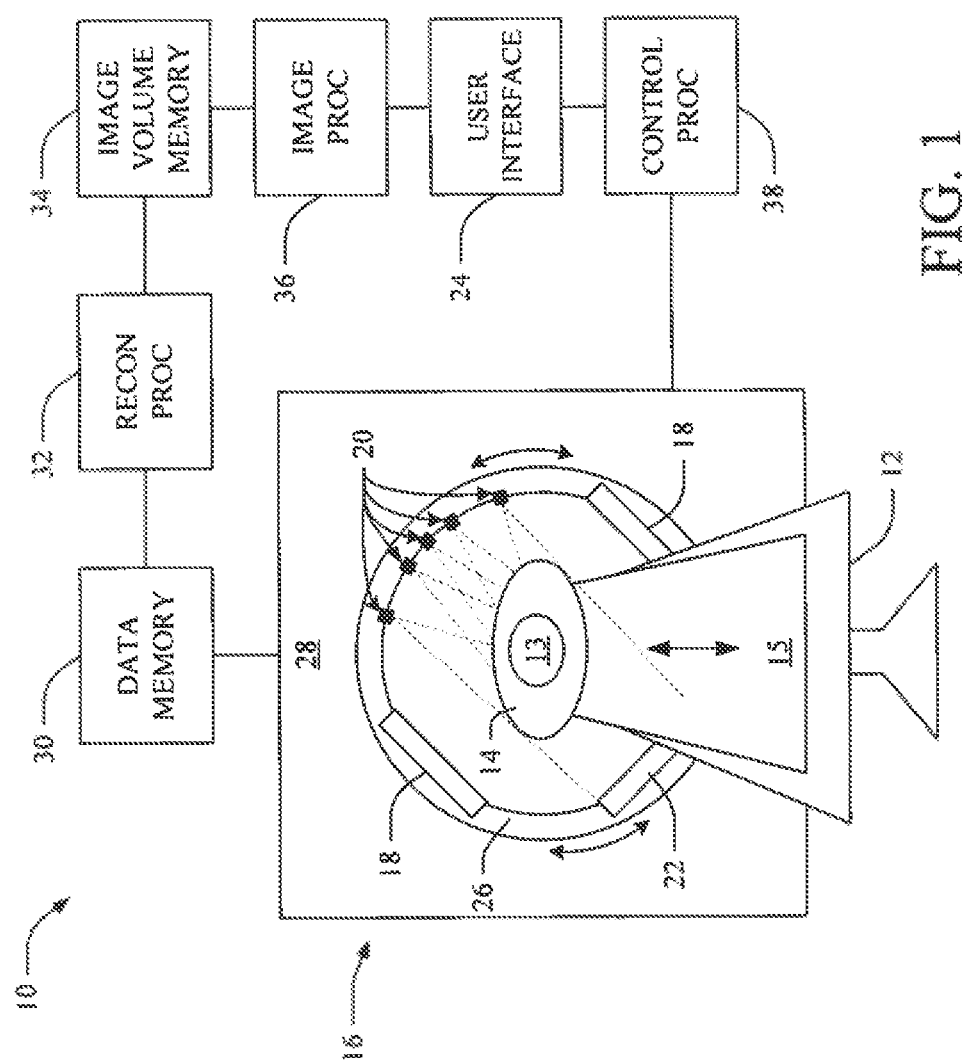
FIG. 1 illustrates an imaging system that includes a subject support, such as a table or couch, which is selectively positionable up and down as well as along the axis of the table, to position a subject being imaged or examined at a desired height, for instance, so that a volume of interest (VOI) of the patient is centered about a longitudinal axis of the imaging system.

The systems and methods described herein relate to overcoming the problem of the small size of flat panel detectors by providing multiple small x-ray sources distributed in an arc around the rotating gantry opposite the flat panel detector. With reference to FIG. 1, an imaging system 10 is illustrated and includes a subject support 12, such as a table or couch, which is selectively positionable up and down and along the axis of the table to position a subject being imaged or examined at a desired height and longitudinal position, for instance, so that a volume of interest (VOI) 13, e.g., the heart, of the patient 14 is centered about a longitudinal axis of the imaging system. The table includes a pallet 15 that is movable parallel to the longitudinal axis through a rotatable gantry 16, such that the VOI of the patient can be translated into the field of view (FOV) of the imaging system for imaging by detectors 18, and, optionally, by a plurality of x-ray sources, such as carbon nanotube (CNT) X-ray sources 20 with electron emitters (not shown), and a flat panel CT or X-ray detector 22. Detectors 18 may be employed in conjunction with any suitable or desired imaging modality. In one embodiment, detectors 18 are gamma cameras or the like, such as are employed in a SPECT imaging system.

A motive power source (not shown), such as a motor, selectively drives the pallet parallel to the longitudinal axis to position the VOI in the FOV. Detected patient image data (e.g., nuclear and/or CT data) is received by a workstation (not shown), which includes appropriate hardware and software for performing image reconstruction and the like to generate images for viewing by an operator on a user interface 24.

An inner gantry structure 26 is rotatably mounted on the outer gantry structure 28 for stepped or continuous rotation. The nuclear detector heads 18 rotate as a group about the subject with the rotation of the rotating gantry structure 26. The nuclear detector heads 18 are radially, circumferentially, and laterally adjustable to vary their distance from the subject and spacing on the rotating gantry 16, 26 to position the detector heads in any of a variety of angular orientations about, and displacements from, the central axis. For example, separate translation devices, such as motors and drive assemblies, are provided to independently translate the detector heads radially, circumferentially, and laterally in directions tangential to the subject (e.g., along linear tracks or other appropriate guides). The embodiments described herein employing two nuclear detector heads can be implemented on a two detector system, a three detector system, or the like. Likewise, the use of three-fold symmetry to adapt the illustrated embodiments to a three detector system is also contemplated.

The system 10 further comprises a data memory 30, coupled to the gantry 16, that stores raw image data (e.g., CT, SPECT, PET, etc.). The data memory is coupled to a reconstruction processor 32 that reconstructs an image volume representation of the scanned VOI 13. In one embodiment, the reconstruction processor 32 reconstructs multiple image volume representations (e.g., CT as well as nuclear scan data). The CT image volume data is then employed to correct for attenuation in the nuclear image volume data, displayed separately, combined with the nuclear image, or the like.

Volume image data is then stored in a volume image memory 34, and an image volume processor 36 employs CT image volume data to generate an attenuation map that is used to correct for attenuation in the nuclear image volume data. A corrected PET or SPECT image volume is then presented to an operator on the user interface 24. Additionally, a CT image volume can be displayed on the user interface.

The user interface 24 is further coupled to a control processor 38, which activates the CNT x-ray sources 20 according to a desired or predefined pulsing pattern during CT acquisition. Moreover, the control processor can selectively alternate through fewer than all of the x-ray sources when, for instance, the cross-section of the patient is small enough that fewer than all sources are required for CT data acquisition using a 180° rotation of the gantry 16, e.g., a head scan. Determination of VOI volume can be automated such as by employing one or more sensors (not shown), or may be user-entered (e.g., using the user interface or the like). In another embodiment, VOI volume can be based on an initial portion of a CT scan of the VOI, thereby providing for real-time optimization of pulsing pattern.

The arc spanned by the x-ray sources 20 is sufficient that x-rays from the plurality of sources that are received by the flat panel detector span the entire maximum cross-sectional dimension of the patient (e.g., a torso of a patient or the like). More specifically, small fixed-anode x-ray tubes are employed in the sources 20, which require much less cooling than larger conventional tubes. Carbon nanotube emitters (not shown) on the x-ray tubes have rapid switching rates (e.g., on the order of a microsecond), which enables rapid sweeping of the x-ray tube that is active compared to the rotational speed of the gantry. Note also that because only one x-ray tube is ON at a time, each x-ray tube is only ON for a fraction of the total x-ray time. For example, in a system with five x-ray tubes, each tube is ON for only 1/5th of the total x-ray irradiation period, which simplifies cooling of the respective sources. It will be appreciated, however, that although FIG. 1 depicts five CNT sources 20, that any suitable number of CNT sources may be employed.

The x-rays need not cover the patient torso uniformly. Rather, as a general proposition, the larger the x-ray flux, the higher the image quality of the image that can be reconstructed. Because the VOI is typically positioned in the center of rotation, it is advantageous to have a higher x-ray density through the center of the imaged VOI than the periphery. This avoids truncation while minimizing patient radiation dose. Additionally, x-ray sources may be selectively activated as a function of the size of the patient or imaged body part. For instance, all five sources may be activated when scanning a large or adult patient, whereas the three central sources may be activated, and the two outer sources remain inactive, during scanning of a small or pediatric patient, an adult head or the like.

Signal detected by the detector 22 can be combined or aggregated to facilitate readout. For instance, the detector 22 can be divided into a grid or the like, and all detected x-rays in a given area (e.g., 1 mm×1 mm or the like) in a give time period, t, may be summed to integrate the detected x-ray energy for analysis.

In one embodiment, the nuclear detector heads are SPECT detector heads. In SPECT imaging, a projection image representation is defined by the radiation data received at each coordinate on the detector head. In SPECT imaging, a collimator defines the rays along which radiation is received.

In another embodiment, the nuclear detector heads are PET detector heads. In PET imaging, the detector head outputs are monitored for coincident radiation events on two heads or a detector ring. From the position and orientation of the heads and the location on the faces at which the coincident radiation is received, a ray or line of response (LOR) between the coincident event detection points is calculated. This LOR defines a line along which the radiation event occurred. In both PET and SPECT, the radiation data from a multiplicity of angular orientations of the heads is then reconstructed into a volumetric image representation of the volume of interest.

In another embodiment, the multiple CNT sources and the detector are employed in conjunction with a magnetic resonance imaging (MRI) system.

The CNT sources 20 rotate around the FOV such that both CT and emission imaging FOVs are coincident or overlapping with limited or no movement of the pallet 15. The flat panel detector 22 is placed in a symmetric geometry relative to the rotation center so that the combined CT FOV from the end sources is sufficient to image patients without truncation. Additionally, the flat panel detector facilitates generating high-resolution radiographic data that can be interpreted as radiograms. Thus, system 10 is a multi-modality system that eliminates or reduces registration problems between nuclear imaging (e.g., SPECT, PET, etc.) and CT or other modality images, since the displacement between the two imaging planes is significantly reduced or eliminated compared to in-line systems, characterized by a different longitudinal position for the nuclear imaging and CT imaging part of the system. This also reduces the requirements on the room size for a combined scanner, since the patient support does not need to be extended to two separate imaging systems, e.g., adjacent nuclear and CT gantries. Complexity and cost of the site preparation is thereby reduced, and retroactive installation of SPECT/CT or PET/CT systems in existing facilities is facilitated. Additionally, the pulse frequency of the sources 20 can be increased as desired to increase temporal resolution (but also spatial resolution because the focal spot size might be reduced compared to conventional X-ray sources).

By spreading the x-ray sources over a distance wider than a largest dimension of the imaged patient, the flat panel detector 22 can be reduced in size, facilitating accommodation of conventional motions of the nuclear detectors 18, mitigating clearance issues that may arise if a larger CT detector were used, and the like. Furthermore, no additional cost is associated with the patient table since no modification is required thereto over existing SPECT or PET imaging table configurations (e.g., because the nuclear imaging FOV and the CT imaging FOV are coincident).

In one embodiment, a helical scan is performed using the CNT sources 20 and detector 22. In another embodiment, the sources are axially offset to provide complete scan data of the VOI in approximately 180° of revolution due to the multiplicity of the sources, in plural rotational paths.

In another embodiment, an anti-scatter grid (not shown) is employed between the detector 22 and the patient to reduce X-ray scatter.

Each source 20 pulses a spot on an anode (not shown), and the sequential pulsing of the respective sources generates a continuous x-ray swath while respective sources have a reduced duty cycle, which improves cooling characteristics of the system relative to conventional systems.

In another embodiment, respective sources alternately pulse two or more spots on the anode (e.g., 1-2 mm apart), which reduces local anode temperature and further improves cooling characteristics of the system.

There are several advantages of the system 10 over conventional CT imaging systems. For instance, system 10 improves volume data acquisition speed through reconstruction of the attenuation map from a 180° CT orbit instead of a 360° orbit. Motion correction is improved due to extensive overlap of fan or cone beam projections from different x-ray sources 20, which permits motion correction for the transmission projections measured at different times, such as respiratory motion correction. The system is also adaptable to different patient sizes, since the number of x-ray sources that are actually used may be chosen depending on patient size and gantry geometry. In the example of FIG. 1, for a small patient, three x-ray sources may be used instead of all five. Another advantage of the system 10 is that it reduces radiation dose to the patient. The image quality to be achieved by the system can be chosen depending on the application, e.g. only for attenuation correction or for high-quality image registration, by appropriate choice of the imaging time or number of x-ray sources activated per sweep. High-quality CT images of specially selected parts of the body can be produced by choosing a higher radiation dose for one or more x-ray sources so that the diagnostically relevant organ or parts of the body are reconstructed with better signal to noise ratio or higher count rate, without much higher patient dose. The extension to a multitude of sources in an axial direction avoids overlap in cone beam imaging and allows an overall dose reduction.

Figure 2:
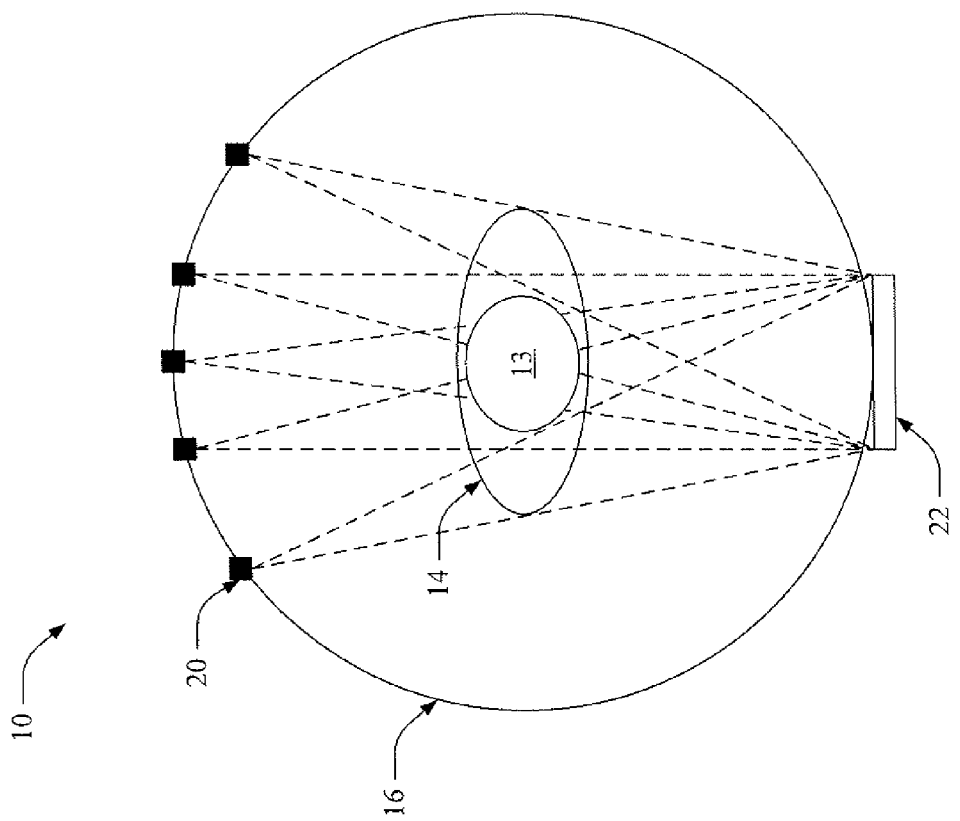
FIG. 2 is an illustration of the system showing overlapping fields of view of the CNT x-ray emitters.

FIG. 2 is an illustration of the system showing overlapping fields of view of the CNT x-ray sources 20. The use of a plurality of small CNT x-ray sources instead of one standard x-ray or CT source reduces X-ray dose to a patient and cooling time for respective CNT x-ray tubes. The x-ray sources 20 are switched on for a short time during each x-ray frame so that the resulting fan beam or cone beam data are interleaved. The resulting data can cover the entire patient and VOI cross-sections during 180° of rotation so that truncation or the need to use a 360° orbit for the transmission measurement is avoided.

The placement of several liquid-cooled X-ray tubes is impeded by space limitations at the gantry. Additionally, the movement of a liquid-cooled tube is complicated and quite expensive. An efficient solution to this problem is the arrangement of fixed anode X-ray sources, especially CNT sources (e.g., CNT field emitters) 20 illustrated in FIG. 2, which includes the placement of several small CNT X-ray tubes with fixed anode targets that are switched in a sequential manner. Compared to rotating anode x-ray tubes, the requirements for the anode current in each of these x-ray sources is markedly reduced due to the dose distribution over several x-ray sources and due to longer imaging time. This in turn allows the application of small fixed-anode sources without liquid cooling systems to avoid an extensive thermal load.

The development of fast-switching CNT sources allows a compact design for such X-ray sources. One advantage of this arrangement is short switching time with X-ray pulses in the range of few microseconds so that synchronization of several sources 20 with the detector acquisition sequence is possible. The sequence of X-ray pulses is programmed in a flexible way, and the selection of the number and the sequence of the sources can be adapted to specific imaging requirements. Additionally, the dose emitted from each of the single sources can be programmed individually, and movement artifacts are reduced due to the short pulse time of each source. Higher dose requirements can be fulfilled with multiple pulses and exact trigger programming. In another embodiment, the acquisition of motion maps with several projections over time can give additional correction information.

The system 10 can be employed in any sort of computed tomography system where the field of view is limited due to a small x-ray detector, such as a flat panel detector 22. The system 10 can be employed for volume imaging, e.g. computed tomography performed using a flat panel detector, such as are provided by Philips Medical Systems.

Figure 3:
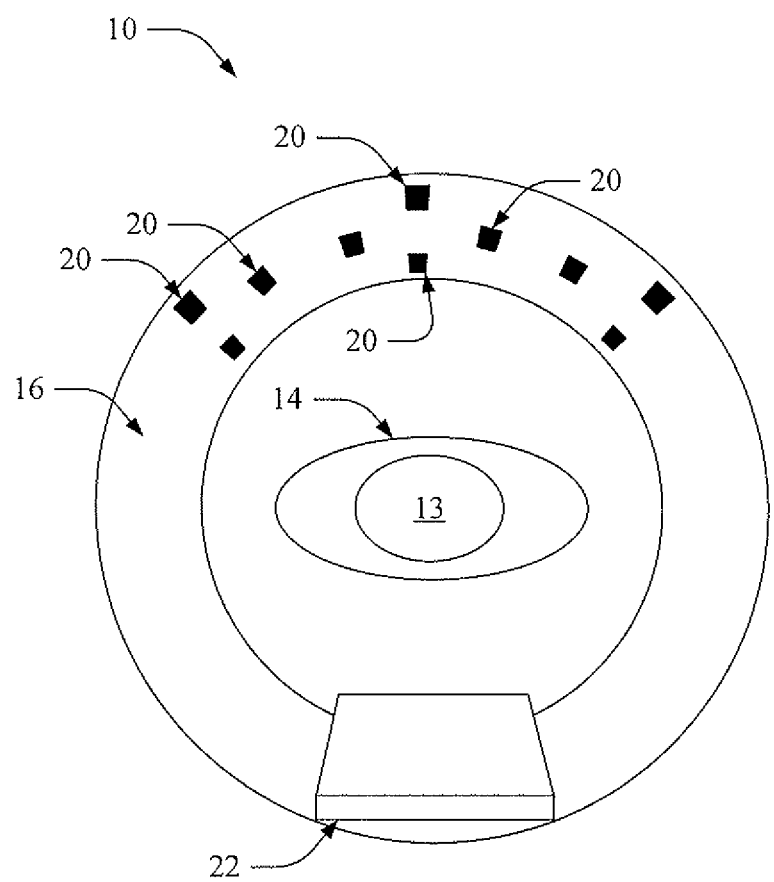
FIG. 3 illustrates an embodiment in which the x-ray emitters are also axially offset.

FIG. 3 illustrates an embodiment in which the x-ray sources 20 are circumferentially and axially offset. This facilitates scanning an axial slab in a single revolution or helical scanning with a faster pitch. In this embodiment, three sets of sources 20 are offset from each other in an axial direction along the gantry 16, and the sets are circumferentially offset relative to each other. Such a matrix of x-ray sources is advantageous for image reconstruction because it provides complete image data for volume reconstruction in a single rotation or partial rotation with no axial patient movement, thereby reducing the patient dose in cone beam CT. It will be appreciated that although FIG. 3 depicts three sets of three sources 20, that any suitable number of sources may be included in each set, and any suitable number of sets of sources may be employed.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

The invention claimed is:

1. A patient imaging system, including:
   a plurality of circumferentially-spaced x-ray sources mounted on a rotatable gantry; and
   a flat-panel X-ray detector mounted on the gantry substantially opposite the x-ray sources;
   wherein the x-ray sources are sequentially pulsed to generate a continuous x-ray swath across a section of a patient including a volume of interest (VOI) as the gantry is rotated around the VOI during computed tomography (CT) acquisition of the VOI;
   wherein a pulsing sequence for the x-ray sources is a function of a VOI profile generated as a function of CT data acquired during an initial portion of the CT acquisition of the VOI, and wherein the pulsing sequence is optimized in real-time.

2. The system according to claim 1, wherein respective X-ray sources direct a cone-shaped X-ray beam to the X-ray detector.

3. The system according to claim 1, wherein respective X-ray sources include carbon nanotube (CNT) x-ray tubes.

4. The system according to claim 1, further comprising nuclear detectors, mounted to the gantry, that are at least one of single photon emission computed tomography (SPECT) detectors or positron emission tomography (PET) detectors.

5. The system according to claim 4, further comprising a processor that employs CT data detected by the detector to correct attenuated scan data detected by the nuclear detectors.

6. The system according to claim 1, wherein the plurality of x-ray sources is arranged in a matrix pattern including multiple axially-spaced rows of CNT x-ray sources, the rows being circumferentially spaced from each other.

7. The system according to claim 1, wherein each x-ray source is pulsed for a period on the order of approximately 1 μs.

8. The system according to claim 1, wherein each x-ray source is pulsed according to a pre-programmed schedule.

9. The system according to claim 1, wherein the x-ray sources include at least three x-ray sources that span a distance greater than the largest cross-sectional distance of the patient.

10. The system according to claim 1, wherein the detector has a width that is approximately half of the largest cross-sectional dimension.

11. The system according to claim 1, wherein respective electron emitters are pulsed to sequentially target multiple focal spots on an anode positioned between the electron emitters and the VOI.

12. The system according to claim 1, wherein the swath of x-rays has a higher x-ray intensity through the VOI and a lower intensity through regions of the patient outside the VOI.

13. A method of CT imaging using the system of claim 1, including:
   sequentially pulsing the plurality x-ray sources to generate a continuous x-ray swath across the patient;
   receiving x-rays at the flat panel detector to acquire CT scan data;
   reconstructing the CT scan data into CT image data; and
   employing the CT image data to correct for attenuation in nuclear image data.

14. A method of CT imaging, including:
   sequentially pulsing a plurality of circumferentially-spaced x-ray sources coupled to a rotatable gantry to generate a continuous swath of x-ray across a transverse section of a patient that includes a VOI;
   receiving x-rays at a flat panel detector to the gantry opposite the x-ray sources to acquire CT scan data; and
   reconstructing the CT scan data into CT image data;
   wherein a pulsing sequence for the plurality of circumferentially-spaced x-ray sources is a function of a VOI profile that is generated as a function of CT data acquired during an initial portion of the CT acquisition of the VOI.

15. The method according to claim 14, further including:
   concurrently collecting nuclear image data, the nuclear image data being reconstructed into a nuclear image.

16. The method according to claim 15, further including employing the CT image data to correct for attenuation in the nuclear image data.

17. The method according to claim 14, further comprising employing fewer than all of the plurality of x-ray sources when the VOI has a volume that is below a predetermined threshold volume.

18. The method according to claim 14, wherein the plurality of x-ray sources are both axially and circumferentially spaced apart on the gantry, and further including:
   collecting a full volume data set of the VOI in 180° of rotation.

19. The method according to claim 14, further including:
   controlling the x-ray sources to pass more radiation through the VOI than through other parts of the patient outside the VOI.

20. The method according to claim 14, wherein the VOI profile is determined by one or more of sensors, manual input, or an initial portion of a scan of the VOI.

21. The method according to claim 14, wherein a pulsing sequence for the x-ray sources is a function of a desired image resolution.

22. A computer readable medium or processor carrying software to execute instructions for performing the method of claim 14.

23. An apparatus for CT imaging, including:
   a control processor that sequentially pulses a plurality of circumferentially-spaced CNT x-ray sources coupled to a rotatable gantry to generate a continuous x-ray across a VOI;
   a flat-panel detector that receives x-rays to acquire CT scan data; and
   a reconstruction processor that reconstructs the CT scan data into CT image data;
   wherein a pulsing sequence for the plurality of circumferentially spaced CNT x-ray sources is a function of a VOI profile generated from at least one of sensor information, manual input, or initial VOI scan data, as a function of CT scan data of the VOI acquired during an initial portion of CT acquisition.

* * * * *